(12) United States Patent
Glukhovsky et al.

(10) Patent No.: US 7,140,766 B2
(45) Date of Patent: Nov. 28, 2006

(54) DEVICE, SYSTEM AND METHOD FOR TEMPERATURE SENSING IN AN IN-VIVO DEVICE

(75) Inventors: Arkady Glukhovsky, Santa Clarita, CA (US); Gavriel Meron, Petach Tikva (IL); Gavriel J. Iddan, Haifa (IL)

(73) Assignee: Given Imaging Ltd., Yoqneam (IL)

( * ) Notice: Subject to any disclaimer, the term of this patent is extended or adjusted under 35 U.S.C. 154(b) by 0 days.

(21) Appl. No.: 10/643,086

(22) Filed: Aug. 19, 2003

(65) Prior Publication Data

US 2004/0109488 A1 Jun. 10, 2004

Related U.S. Application Data

(63) Continuation-in-part of application No. 09/806,714, filed as application No. PCT/IL00/00470 on Aug. 3, 2000, now Pat. No. 6,607,301.

(30) Foreign Application Priority Data

Aug. 4, 1999 (IL) .................................. 131242

(51) Int. Cl.
*G01K 7/00* (2006.01)
(52) U.S. Cl. ..................... 374/175; 374/121
(58) Field of Classification Search ............. 374/175, 374/117, 121, 141; 250/339.04, 352; 348/243, 348/245, 909, 45, 65; 600/549, 474, 109, 600/117, 160; 327/512, 513
See application file for complete search history.

(56) References Cited

U.S. PATENT DOCUMENTS

| | | | | |
|---|---|---|---|---|
| 2,710,899 A | * | 6/1955 | Marsden, Jr. et al. | ........ 374/175 |
| 2,768,266 A | * | 10/1956 | Marsden, Jr. | ................ 374/175 |
| 3,882,384 A | * | 5/1975 | List | .............................. 327/512 |
| 3,937,086 A | | 2/1976 | Von Thuna | |
| 3,971,362 A | | 7/1976 | Pope et al. | |
| 4,177,800 A | | 12/1979 | Enger | |
| 4,180,736 A | | 12/1979 | Goodman | |
| 4,246,784 A | | 1/1981 | Bowen | |
| 4,278,077 A | | 7/1981 | Mizumoto | |
| 4,643,587 A | | 2/1987 | Makabe et al. | |
| 4,646,723 A | | 3/1987 | Arakawa | |
| 4,646,724 A | * | 3/1987 | Sato et al. | ................... 600/109 |
| 4,689,621 A | | 8/1987 | Kleinberg | |
| 4,744,672 A | | 5/1988 | Tursky et al. | |
| 4,786,969 A | * | 11/1988 | Shouji et al. | ................ 348/243 |
| 4,807,633 A | | 2/1989 | Fry | |
| 4,844,076 A | | 7/1989 | Lesho et al. | |
| 4,885,077 A | | 12/1989 | Karakelle et al. | |

(Continued)

FOREIGN PATENT DOCUMENTS

DE 34 40 177 5/1986

(Continued)

OTHER PUBLICATIONS

Jones, B.K., "Electrical Noise Thermometer," Appl. Phys. vol. 16, No. 1, pp. 99-102 (May 1978).*

(Continued)

*Primary Examiner*—Diego Gutierrez
*Assistant Examiner*—Mirellys Jagan
(74) *Attorney, Agent, or Firm*—Pearl Cohen Zedek Latzer, LLP

(57) ABSTRACT

A device, method and system for sensing the temperature or temperature change of an environment. A typically in-vivo device includes an image sensor. The device may sense the dark current noise of the image sensor, and calculate the temperature or a temperature change of the image sensor.

7 Claims, 5 Drawing Sheets

U.S. PATENT DOCUMENTS

| | | | |
|---|---|---|---|
| 4,891,970 A | 1/1990 | Remboski, Jr. | |
| 4,936,823 A | 6/1990 | Colvin et al. | |
| 5,047,863 A * | 9/1991 | Pape et al. | 348/247 |
| 5,098,197 A | 3/1992 | Shepard et al. | |
| 5,109,870 A | 5/1992 | Silny et al. | |
| 5,278,656 A * | 1/1994 | Hynecek et al. | 348/65 |
| 5,279,607 A | 1/1994 | Schentag et al. | |
| 5,354,130 A | 10/1994 | Seppa et al. | |
| 5,368,027 A | 11/1994 | Lubbers et al. | |
| 5,508,740 A | 4/1996 | Myaguchi et al. | |
| 5,604,531 A * | 2/1997 | Iddan et al. | 600/109 |
| 5,640,235 A | 6/1997 | Iwasaki | |
| 5,697,384 A | 12/1997 | Miyawaki et al. | |
| 5,746,511 A | 5/1998 | Eryurek et al. | |
| 5,819,736 A | 10/1998 | Avny et al. | |
| 5,833,603 A | 11/1998 | Kovacs et al. | |
| 5,853,005 A | 12/1998 | Scanlon | |
| 5,993,378 A | 11/1999 | Lemelson | |
| 6,074,349 A | 6/2000 | Crowley | |
| 6,148,152 A * | 11/2000 | Cazier et al. | 348/243 |
| 6,165,128 A | 12/2000 | Céspedes et al. | |
| 6,184,511 B1 | 2/2001 | Yamashita | |
| 6,222,454 B1 * | 4/2001 | Harling et al. | 250/339.04 |
| 6,240,312 B1 | 5/2001 | Alfano et al. | |
| 6,267,501 B1 * | 7/2001 | Wand et al. | 348/243 |
| 6,433,333 B1 * | 8/2002 | Howard | 250/339.04 |
| 6,584,348 B1 | 6/2003 | Glukhovsky | |
| 6,607,301 B1 * | 8/2003 | Glukhovsky et al. | 374/175 |
| 6,614,562 B1 * | 9/2003 | Minemier | 358/483 |
| 6,641,529 B1 * | 11/2003 | Kuranishi | 600/109 |
| 6,927,795 B1 * | 8/2005 | Cazier et al. | 348/243 |
| 2001/0035902 A1 * | 11/2001 | Iddan et al. | 348/65 |
| 2002/0103417 A1 | 8/2002 | Gazdzinski | |
| 2002/0146368 A1 | 10/2002 | Meron et al. | |
| 2002/0175269 A1 * | 11/2002 | Krymski | 250/208.1 |
| 2003/0002624 A1 * | 1/2003 | Rinaldi et al. | 378/98.8 |
| 2003/0040685 A1 | 2/2003 | Lewkowicz et al. | |
| 2003/0077223 A1 | 4/2003 | Glukhovsky et al. | |
| 2003/0167000 A1 | 9/2003 | Mullick et al. | |
| 2003/0208107 A1 | 11/2003 | Rafael | |
| 2004/0036776 A1 * | 2/2004 | Wakabayashi et al. | 348/207.99 |
| 2004/0099920 A1 * | 5/2004 | Rossi et al. | 257/448 |
| 2004/0122315 A1 * | 6/2004 | Krill | 600/549 |
| 2004/0170215 A1 * | 9/2004 | Rossi et al. | 374/121 |

FOREIGN PATENT DOCUMENTS

| | | |
|---|---|---|
| EP | 0 667 115 | 8/1995 |
| GB | 2353166 | 2/2001 |
| JP | 57-45833 | 3/1982 |
| JP | 4-109927 | 4/1992 |
| JP | 4109927 | 4/1992 |
| JP | 5015515 | 1/1993 |
| JP | 6-114036 | 4/1994 |
| JP | 8-201170 | 8/1996 |
| JP | 9-45893 | 2/1997 |
| WO | WO 9930610 A1 * | 6/1999 |
| WO | WO 01/50941 | 7/2001 |

OTHER PUBLICATIONS

Holst, G.C., "CCD arrays cameras and displays", Second Edition (SPIE O.E. Press and JCD Publ.), chap. 4. pp. 102-145 (1998, no month).*

Ritter, T., "Random Electrical Noise: A Literature Survey, Research Comments from Ciphers By Ritter," www.io.com, (Dec. 1999).*

Eric R. Fossum, Digital Camera System on a Chip, IEEE Micro, May-Jun. 1998, pp. 8-15.*

BBC News Online—Pill camera to 'broadcast from the gut', Feb. 21, 2000, www.news.bbc.co.uk.

Wang, et al., "Integrated Micro-Instrumentation for Dynamic Monitoring of the Gastro-Intestinal Tract", Presented at IEEE Instrumentation and Measurement Technology Conference, May 2002, Anchorage, Ak, USA. www.see.ed.ac.uk/Naa.publications.html.

The Radio Pill, Rowlands, et al., British Communications and Electronics, Aug. 1960, pp. 598-601.

Video Camera to "TAKE"—RF System lab, no date available, (1 page).

Wellesley company sends body montiors into space—Crum, Apr. 1998, Boston Business Journal, p. 7.

Wireless transmission of a color television moving image from the stomach using a miniature CCD camera, light source and microwave transmitter. Swain CP, Gong F, Mills TN. Gastrointest Endosc 1997;45:AB40, (Apr. 1997).

Photobit PB-159 DX Product Specification, Aug. 1998 (Version 3.0), (1 pg).

"Robots for the future"—Shin-ichi, et al., Nov. 29, 2001, (12 pages).

NORIKA3, Dec. 24, 2001, (14 pages), www.rfnorika.com.

European Search Report for EP 04 01 9677 mailed on Nov. 4, 2005.

Japanese Office Action for JP Application No. 2001-514821—prior art search record, mailed on Feb. 21, 2006.

* cited by examiner

DEVICE, SYSTEM AND METHOD FOR TEMPERATURE SENSING IN AN IN-VIVO DEVICE

RELATED APPLICATION DATA

The present application is a continuation-in-part of U.S. application Ser. No. 09/806,714 filed on Oct. 9, 2001 now U.S. Pat. No. 6,607,301 and entitled "DEVICE AND METHOD FOR DARK CURRENT NOISE TEMPERATURE SENSING IN AN IN-VIVO IMAGING DEVICE," which in turn claims priority from International Application number PCT/IL00/00470 filed 3 Aug. 2000 and Israeli application number 131242 filed Aug. 4, 1999.

FIELD OF THE INVENTION

The present invention relates to a method and system for measuring the temperature of an environment, such as the interior of the body.

BACKGROUND OF THE INVENTION

In many circumstances it is important to measure the temperature inside a material body. Such circumstances may occur during industrial processes or exploration and analysis processes, such as in geophysical probing or in medical diagnostics and treatment of internal parts of the body.

Conventional thermometry and absolute thermometry are known methods for measuring temperature.

Conventional thermometry is based upon the temperature coefficient of properties of materials, such as resistance or mechanical expansion.

Absolute thermometry is a method which directly measures thermal energy of a sensor resistance. This method is based upon the known physical phenomenon of spontaneous thermal noise arising from the Brownian motion of ionized molecules within a resistance.

Thermal noise, which can be discussed in terms of thermal current, provides a direct measurement of temperature on a thermodynamic scale, thus the Boltzmann constant defines the temperature. The phenomenon of thermal noise is derived, for example, in the book: *CCD arrays cameras and displays* by Holst G. C., p. 128, $2^{nd}$ edition, SPIE Press, 1998. A formula that may be used to define thermal current is, for example:

$$<i_n^2> = k\, T\, C$$

where k is the Boltzmann constant, T is the temperature of a sensor, and C is the capacitance of the sensor. Thus the magnitude of the signals produced by the thermal current is directly proportional to the square root of the temperature of the sensor. Experiments have indicated that the signal doubles with the increase of 7° C. (degrees Centigrade), which means that a resolution better than 0.1° C. is achieved.

In image sensors, the thermal current produced in an operating photodetector device, when no optical radiation impinges on the detector, is called "dark current". In CCD cameras dark current is basically charge which accumulates in the CCD pixels due to thermal noise. The effect of dark current is to produce an additive quantity to the electron count in each pixel.

U.S. Pat. No. 3,937,086 to von Thuna, U.S. Pat. No. 5,354,130 to Seppa et al. and U.S. Pat. No. 5,098,197 to Shepard et al. all describe devices for measuring the absolute temperature of a body material by receiving and analyzing the thermal noise of the body material.

U.S. Pat. No. 4,246,784 to Bowen describes a method for noninvasive temperature measurement of th interior of a body using the acoustic thermal noise spectrum of the measured body.

None of these temperature measurement methods utilize an image sensor to measure the thermal noise of a body material.

SUMMARY OF THE INVENTION

Embodiments of the present invention provide a method and system for sensing the temperature or temperature change of an environment, such as inside a body, by calculating the temperature of an image sensor in the environment and deducing the environment's temperature from the image sensor's calculated temperature. The temperature or temperature change of the image sensor may be calculated by measuring its generated dark current noise.

Embodiments of the present invention may use an image sensor, in which thermal noise is easily detectable, for deducing the temperature of a material body. Furthermore, according to embodiments of the invention, a single sensor is utilized for obtaining visual data and data relating to the temperature of the environment. Thus, diverse information about an environment can be obtained utilizing a single sensing device.

There is thus provided according to an embodiment of the present invention a method for sensing the temperature of an environment comprising the steps of introducing into an environment an image sensor having an image sensing module, sensing the dark current noise of the image sensor, calculating the temperature of the image sensor, calculating the temperature of the environment and optionally displaying the calculated environment temperature.

It will be appreciated that the term "environment" when used herein relates to a space enclosed within walls in which it is desired to measure the temperature of the space and/or of the walls.

The temperature of the image sensor is indicative of the temperature of it's immediate surroundings and, relying on known factors such as heat distribution, distance from the image sensor, etc., the temperature of further areas can also be calculated.

The image sensors utilized in embodiments of the invention can be for example digital cameras or video cameras such as vidiocon, CCD cameras or Complementary Metal Oxide Semiconductor (CMOS) cameras.

Embodiments of the present invention further provide a system for sensing the temperature of an environment. The system comprises an image sensor having an image sensing module in communication with an integrating unit for detecting the dark current of the image sensor image sensing module and for calculating the temperature of the image sensor. The integrating unit may further calculate the temperature of the environment or the temperature of the environment may be calculated, based on data from the integrating unit, by a separate unit that is in communication with the integrating unit.

The integrating unit may have an amplifying function for amplifying signals received from the image sensor.

The communication between the image sensor and integrating unit can be optionally controlled according to the illumination conditions, optionally through a switch which enables communication only during periods in which the sensor is not illuminated.

BRIEF DESCRIPTION OF THE DRAWINGS

The present invention will be understood and appreciated more fully from the following detailed description taken in conjunction with the figures in which.

DETAILED DESCRIPTION OF THE INVENTION

In the following detailed description, numerous specific details are set forth in order to provide a thorough understanding of the invention. However, it will be understood by those of ordinary skill in the art that the invention may be practiced without these specific details. In other instances, well-known methods, procedures, components, units and/or circuits have not been described in detail so as not to obscure the invention.

Analytical and diagnostic processes which utilize image sensors to monitor environments could benefit from obtaining information relating to the temperature of the environment, as a local change of temperature can indicate an irregular event.

For example, some embodiments described in U.S. Pat. No. 5,604,531, which is assigned to the common assignees of the present application, describe a swallowable device that can pass through the entire digestive tract and operate as an autonomous video endoscope. U.S. Pat. No. 5,604,531, is hereby incorporated by reference. The swallowable device may include a) a camera system, b) an optical system for imaging an area of interest onto the camera system and c) a transmitter which transmits the video output of the camera system and/or other data. Visual data obtained by the swallowable device can indicate, inter alia, the location of pathologies in the gastrointestinal tract. Also a local change of temperature in the gastrointestinal tract can be indicative of a pathology. Thus, the information obtained by visual means can be complemented and focused by information relating to local temperature in the gastrointestinal tract. An external receiving, processing and/or display system may receive, process and or display data received from the device.

The method of an embodiment of the present invention may enable simultaneous visual monitoring and temperature sensing.

Figure 1:
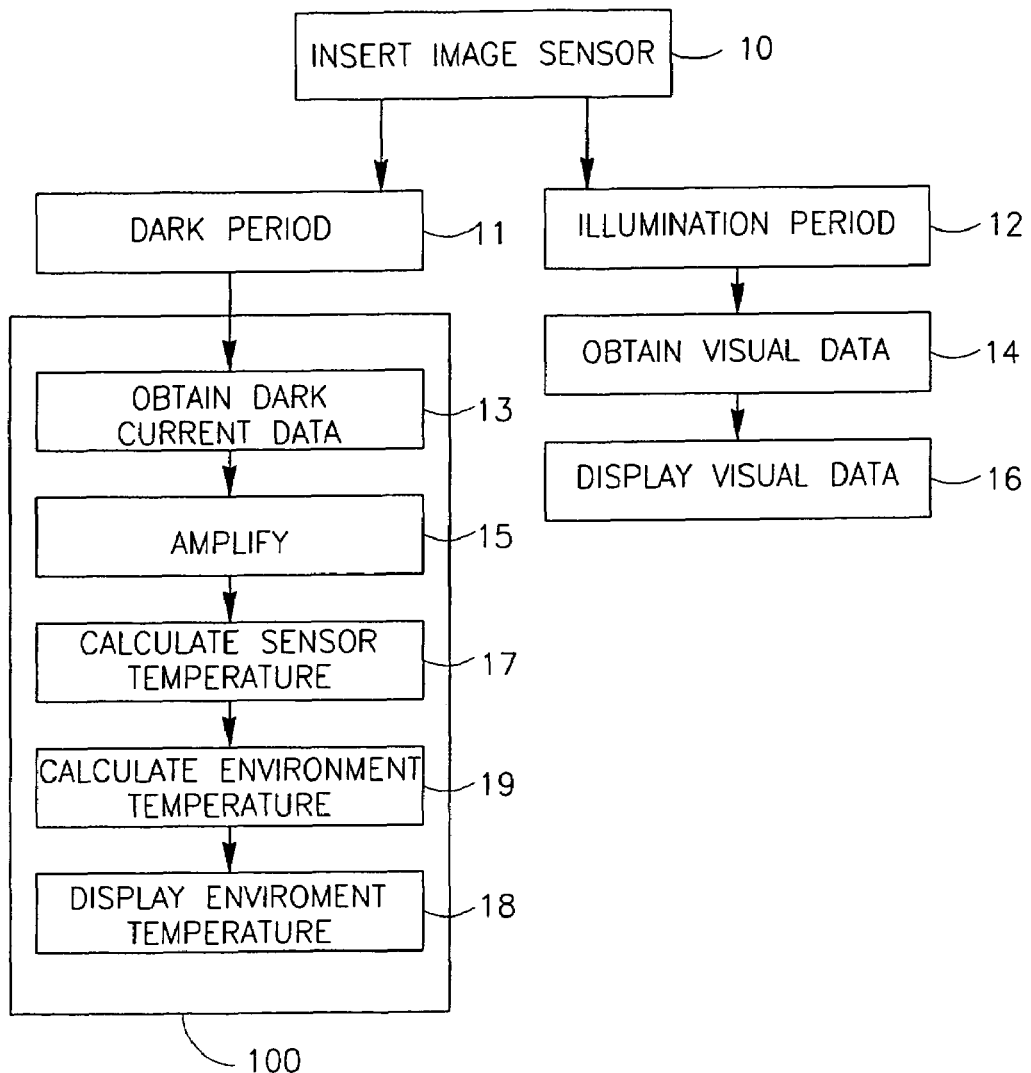
FIG. 1 is a block diagram representing an embodiment of the method according to an embodiment of the invention.

The method is schematically described by a block diagram shown in FIG. 1. An image sensor, such as in the above mentioned swallowable device, is inserted 10 into an environment, such as the gastrointestinal tract. The swallowable device 30 is typically capsule shaped, but may have other shapes and need not be swallowable.

Illumination is provided intermittently, either by elements connected to the image sensor itself or by external sources. When illumination is provided 12 only visual data is obtained 14 and displayed 16. A process for obtaining and displaying visual data is described, for example, in the above mentioned U.S. Pat. No. 5,604,531.

In an intermittent dark period 11 an integrating unit 100 is activated to obtain dark current data 13 from the image sensor, though it is not imperative to shut off illumination in order to obtain data relating to dark current noise, as will be discussed in more detail below.

Figure 5:
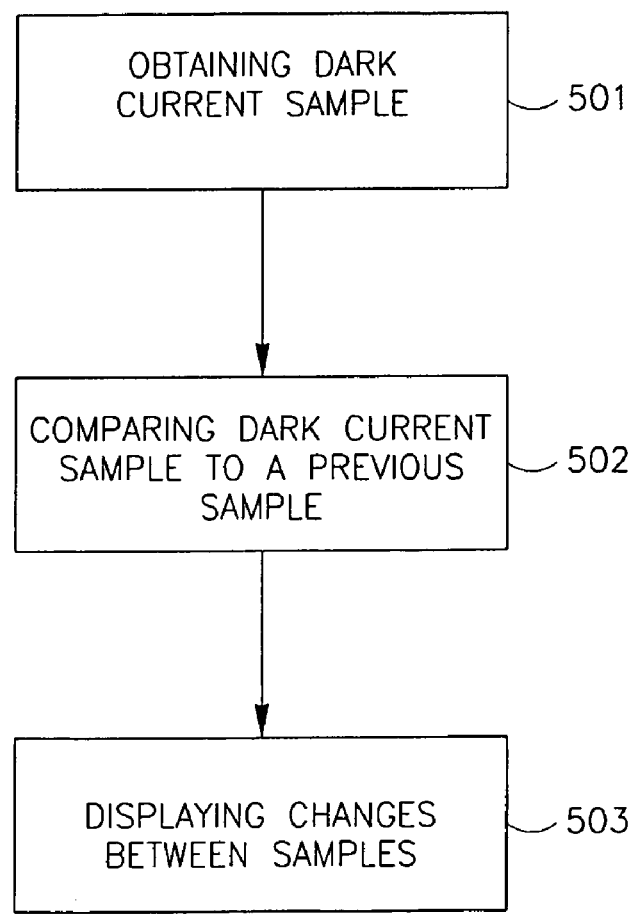
FIG. 5 is a block diagram representing an embodiment of a method according to an embodiment of the invention.

The integrating unit 100 is a processor capable of amplifying the obtained data 15, if necessary, and calculating the image sensor temperature 17 using the known equations derived for thermal noise. It will be appreciated that these equations are an approximation of a complex phenomenon and that calibration should be employed in order to deduce the actual calculations that will be applied. According to some embodiments, for example, as schematically illustrated in FIG. 5, the image sensor temperature and/or the environment temperature need not be calculated. Rather, a difference in dark current measurements (which are typically indicative of temperature changes) may be determined. Thus, a difference in temperature changes may be determined or calculated. In one embodiment, the amount of temperature change need not be determined, but rather that a temperature change occurred, and, possible, the direction of temperature change (hotter, cooler).

According to an embodiment of the invention a dark current data sample may be obtained (501), for example, according to a predetermined schedule or by any other appropriate method (for example, as discussed below). Dark current data sample may be compared, for example by using a change detector, to a previous dark current sample (502). A difference between two samples can indicate a temperature change. According to some embodiments a sample may be compared to an average or other manipulation of several previous samples. Thus, the actual temperature of the image sensor and/or of the body lumen environment need not be calculated.

According to some embodiments a change in dark current data may be displayed (503). According to other embodiments only a change which is above a predetermined threshold may be displayed. According to yet further embodiments a change which is over a predetermined threshold may be used as a trigger for changing the activity of other elements of the system. For example, a swallowable device, such as described in the above mentioned U.S. Pat. No. 5,604,531, may include an integrating unit or other calculating unit which may be capable of detecting a change in dark current data, as described above. The integrating unit may be in communication with other elements of the device, such as the power supply or the illumination system or transmitter of the device, and an ON or OFF signal may be generated, typically by the integrating unit, to any of these elements in accordance with detected dark current changes. Thus, the operational mode or settings of an in vivo sensor can be altered or activated in response to in vivo temperature. According to certain embodiments, a swallowable device may include a controller or calculating unit for activating or altering the operational mode or settings of the device in response to signals from the integrating unit, Such an embodiment may be useful in some case for example, for saving energy. According to one embodiment after a device or other in-vivo device is swallowed the patient is made to ingest a volume of cold or hot water at regular intervals. According to one embodiment the patient ingests cold or hot water over a period of a few hours, for example, a period in which the device has most probably left the stomach. While the device is in the stomach an ingested volume of cold or hot water may cause a change of temperature in the stomach environment, Once in the small intestine, the effect of a cold or hot drink is no longer felt. According to one embodiment of the invention a change of temperature may be checked at predetermined intervals. While a temperature change (typically above a predetermined threshold) is detected the device may be kept inactive. If a temperature change is not sensed the device may be triggered to activate the device. Thus, the device begins collecting data only when it is close to the large intestine thereby saving energy and allowing effective and complete action of the device in the large intestine.

The environment temperature or a change in environment temperature is then calculated 19, by the integrating unit 100, by a separate unit in communication with the integrating unit 100, or possibly by another unit. Calculations of the environment temperature may be based on the existence of thermal equilibrium between the image sensor and environment. These calculations take into account energy dissipation from the image sensor. Local temperature or the average temperature within the environment may be calculated, depending on specific requirements. The calculated temperature may then be displayed 18.

It will be appreciated that the various calculations and/or detections may be carried out by software or software means executable on computing means such as a computer or similar data processors, microprocessors, embedded processors, microcomputers, microcontrollers etc.

The integrating unit 100 may include separate processors, which need not all be physically connected. Some of the functions carried out by integrating unit 100, such as calculating the image sensor temperature 17 and calculating the environment temperature 19, can be carried out in processors that are external to the environment and that are fed with data from the integrating unit 100 by communication such as by IR or radio. Indeed, if an operator is to note the temperature of the environment, at least the function of displaying the calculated temperature 18 must be performed externally to the environment.

Integrating unit 100 may be in communication with other units to further process and use the data obtained by it. For example, a device, such as described in U.S. Pat. No. 5,604,531, may include a sample chamber for collecting samples from the environment of the digestive tract. The process of collecting a sample can be controlled by integrating unit 100, such that samples are collected only in locations along the digestive tract in which a predetermined temperature is prevalent or in which a certain temperature change has been detected.

Figure 2:
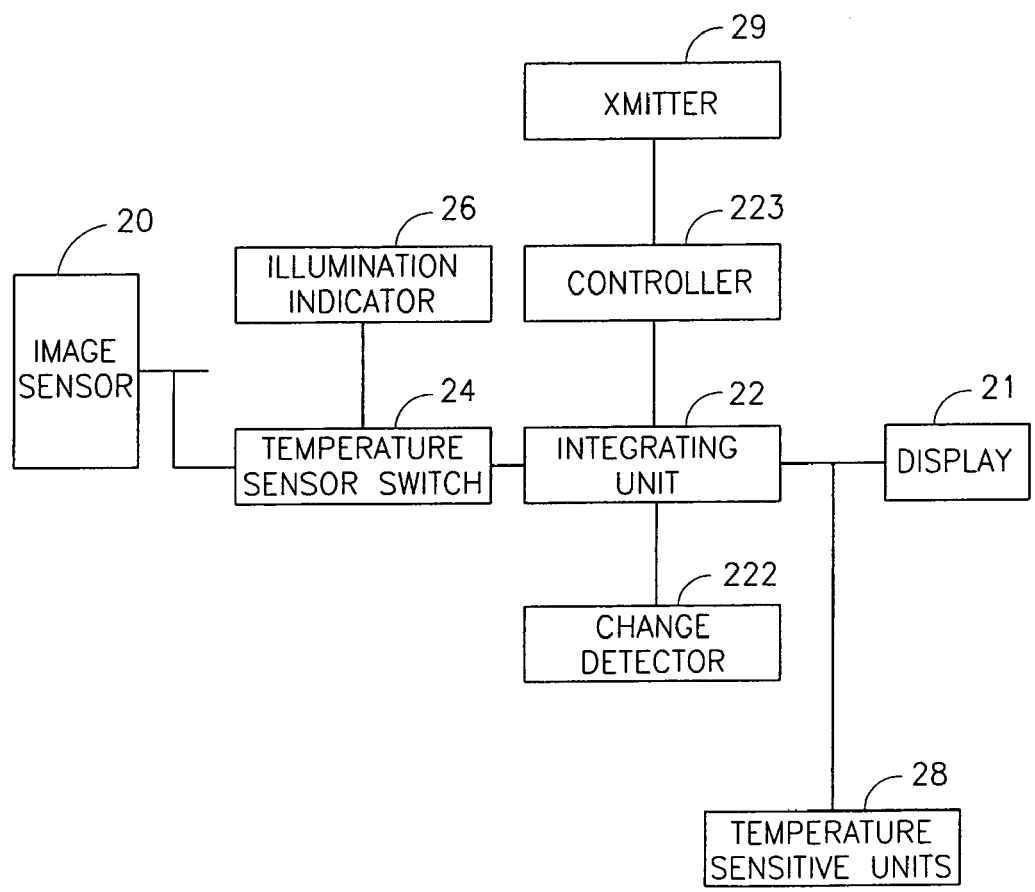
FIG. 2 is a schematic illustration of an embodiment of the system according to an embodiment of the invention.

Reference is now made to FIG. 2, which is a schematic illustration of the system according to an embodiment of the invention. The system includes an image sensor 20 having an image sensing module which includes a pixel array (as demonstrated in FIG. 3) in communication with an integrating unit 22. Communication is enabled by temperature sense switch 24 which is controlled by illumination indicator 26, such that communication is enabled only during dark periods.

When communication between the image sensor 20 and integrating unit 22 is established, integrating unit 22 receives dark current data from image sensor 20.

In an alternate embodiment a switch and/or illumination indicator need not be used. According to some embodiments dark current data may be received from the image sensor 20 continuously or according to a predetermined time schedule. For example, a system in which 25 ms light flashes are followed by 475 ms dark periods, may be programmed to sample dark current data once every dark period. In an alternate embodiment a system may include a dark frame once every so often, e.g., one frame in every 256 frames is not illuminated. According to some embodiments a system may be programmed to sample dark current data -during a dark frame. Other time periods or intervals may be used.

It is possible to calculate the image sensor's 20 temperature or temperature change based on dark current data obtained from a single pixel of the image sensor pixel array, though data obtained from a higher number of pixels may achieve more accurate results. It is therefore possible to keep a portion of the image sensor's 20 pixels of the pixel array, constantly unexposed to illumination, and obtain dark current data from the unexposed pixels, without having to shut off the illumination. Thus simultaneous image capture and and temperature sensing may be carried out.

Thus, dark current data can be obtained also during constant illumination by either covering a portion of the pixels of the pixel array or by having a portion of the pixel array pixels outside of the image field, e.g. the pixels in the periphery of the pixel array.

The integrating unit 22 may be or include a processor capable of amplifying the dark current signal and calculating the image sensor temperature from the dark current signal. It may be capable of calculating the environment temperature from the image sensor temperature and is capable of displaying the calculated environment temperature 21. Integrating unit 22 may control different temperature sensitive units 28, such as a sample chamber, in correspondence with predetermined temperatures or temperature changes. A transmitter 29 may transmit data such as image data, dark current data, temperature data, and/or temperature change data.

The system may also include a change detector 222 (typically in communication with the integrating unit 22) and a controller 225 for activating or altering the operational mode or settings of the device in response to signals from the integrating unit 22 or another unit, The various processing and detecting components described herein, and their functionalities, may be combined over different components than separately shown. For example, a single controller may perform all functionality. In one embodiment control and calculation capability may be included within transmitter 29.

Figure 3:
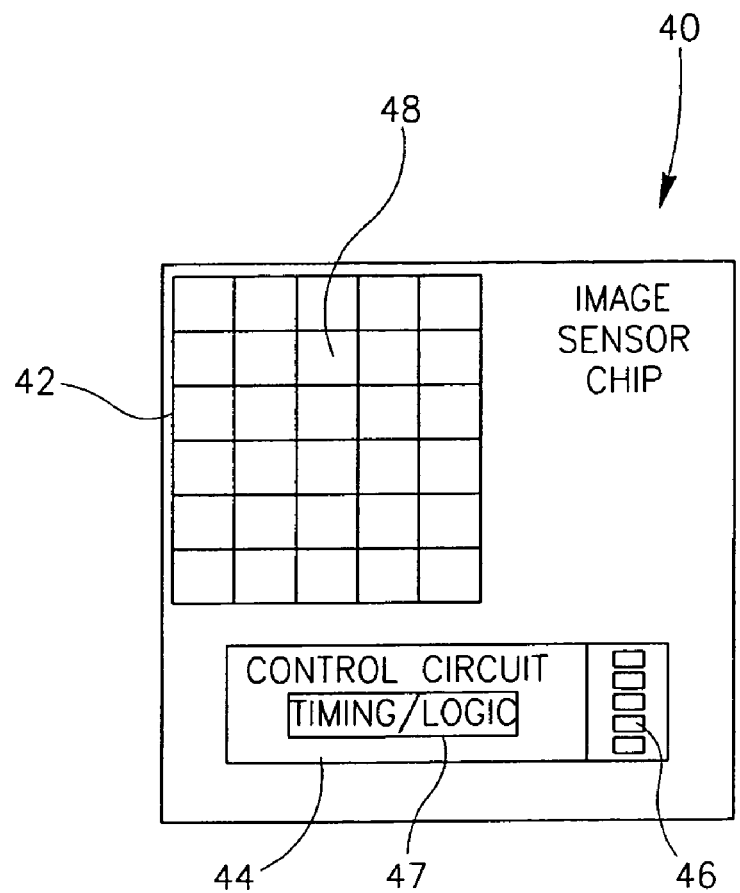
FIG. 3 is a schematic illustration of a functional block layout of the image sensor according to an embodiment of the invention.

Reference is now made to FIG. 3 which is a schematic illustration of a functional block layout of the image sensor according to an embodiment of the invention. The image sensor typically includes a single chip 40 having an image sensing module 42 and a control circuits area 44. The image sensing module 42 includes a pixel array 48 for capturing an image. The control circuits area 44 includes the timing and logic circuitry 47 and AND circuitry 46.

Signals can be received from all the pixels of the pixel array 48. Dark current is received from pixels that are not illuminated or from pixels during a dark period whereas current signals received from an illuminated pixel are the summation of the dark current and light current of the pixel. The accumulation of signals from all the pixels is converted to data which is communicated through a transmitter such as transmitter 29 to the integrating unit for decoding and for displaying a visual representation and/or the temperature derived from the data.

Figure 4:
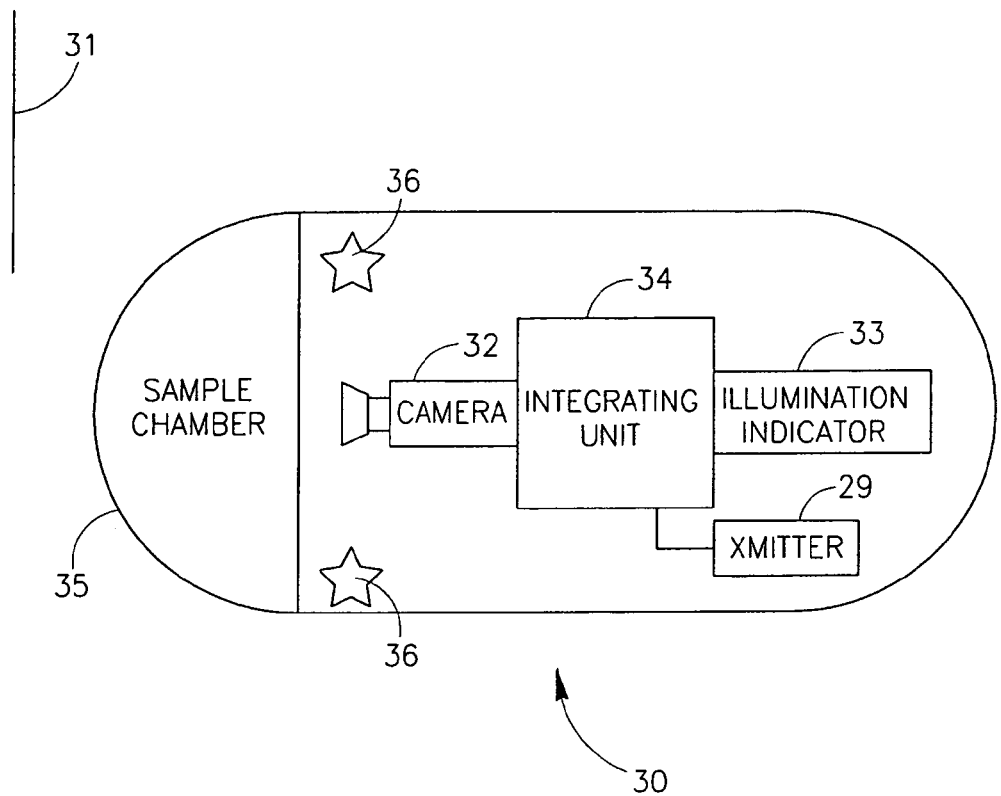
FIG. 4 is a schematic illustration of a medical device comprising the system according to an embodiment of the invention.

The system of an embodiment of the invention will be further described and demonstrated by FIG. 4 which is a schematic illustration of a medical device comprising a system according to an embodiment of the invention.

The medical device illustrated in FIG. 4 is a swallowable device, generally referenced 30. Device 30 which may include components and functionality similar to that described in the above mentioned U.S. Pat. No. 5,604,531, but alternately may be of different construction and include different functionality and components. Swallowable device 30 is typically capsule shaped, but may have other shapes and need not be swallowable. Swallowable device 30 comprises a CMOS camera 32, that is in communication with integrating unit 34. The swallowable device 30 further comprises illuminating elements 36 that are in communication with illumination indicator 33. The gastrointestinal tract walls 31 are illuminated by illuminating elements 36, in intermittent pulses, capturing consecutive images of the gastrointestinal tract walls 31 by camera 32, enabling an operator to view the gastrointestinal tract walls. Communication between camera 32 and integrating unit 34 is enabled in between illumination pulses when illumination indicator 33, sensing the lack of illumination, activates the temperature sense switch (not shown) to an ON position.

Alternatively, the illumination indicator 33 may be activated by the operator to simultaneously turn off the illumination elements 36 and switch the temperature sense switch to an ON position.

Once communication is established between camera 32 and integrating unit 34 dark current signals generated from camera 32 may be received and processed, as described above, by integrating unit 34. The calculated gastrointestinal temperature, or temperature change may be displayed on a display unit external to the gastrointestinal tract. For example, a workstation or personal computer may indicate that a change in temperature occurred, the direction of temperature change, and/or the amount of temperature change. Other body lumens may have temperature or temperature change detected.

All or part of the functionality of receiving dark current data and calculating a temperature or temperature change may be carried out by parts of an external receiving, processing and/or display system, such as a remote personal computer or workstation.

Swallowable device 30 may include a sample chamber 35 for collecting samples from the gastrointestinal tract environment. The collected sample may be cells from the gastrointestinal tract walls or a liquid sample from the gastrointestinal tract environment. The mechanism for collecting samples, which can be any suitable mechanism known in the art, is controlled by integrating unit 34, such that it is activated in accordance with the gastrointestinal tract environment calculated temperature. Alternatively, the mechanism can be controlled by the operator based on the displayed temperature.

It will be appreciated by persons skilled in the art that the present invention is not limited to what has been particularly shown and described hereinabove.

The invention claimed is:

1. A method for calculating a temperature change in vivo, the method comprising:
   introducing in vivo an image sensor having an image sensing module;
   sensing the dark current noise of the image sensing module;
   obtaining a dark current data sample according to a predetermined time schedule during at least one dark period during which the image sensor is not illuminated;
   comparing a dark current data sample of the sensed dark current noise to a previous sample; and
   calculating the temperature change in vivo according to the comparison;
   wherein the image sensor is contained within a capsule.

2. A method according to claim 1, comprising displaying the in vivo temperature.

3. A system for calculating a temperature change in vivo comprising:
   a capsule comprising:
   an image sensor;
   an integrating unit; and
   a change detector;
   said image sensor contained within said capsule and being introduced in vivo; and
   said integrating unit receiving dark current noise samples from the image sensor according to a predetermined time schedule during at least one dark period during which the image sensor is not illuminated, and said change detector detecting changes between said dark current noise samples and calculating the temperature change in vivo according to the changes.

4. A system according to claim 3, wherein communication between said integrating unit amplifies said dark current noise samples received from said image sensor by said integrating unit.

5. A system according to claim 3, wherein said image sensor and said integrating unit are controlled according to an illumination condition.

6. A system according to claim 3, wherein said image sensor senses the dark current noise during a dark period.

7. A system according to claim 3, wherein said image sensor communicates with said controller during periods when said image sensor is not illuminated.

* * * * *